(12) United States Patent
Pruitt et al.

(10) Patent No.: US 7,323,313 B2
(45) Date of Patent: Jan. 29, 2008

(54) METHODS FOR PROTEIN INTERACTION DETERMINATION

(75) Inventors: Steven C. Pruitt, Williamsville, NY (US); Alexander Hastie, Buffalo, NY (US); Lawrence Mielnicki, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 344 days.

(21) Appl. No.: 10/842,741

(22) Filed: May 10, 2004

(65) Prior Publication Data

US 2005/0164214 A1 Jul. 28, 2005

Related U.S. Application Data

(60) Provisional application No. 60/469,342, filed on May 9, 2003.

(51) Int. Cl.
*G01N 33/53* (2006.01)
*C12Q 1/68* (2006.01)
*C12N 15/63* (2006.01)
*C07H 21/02* (2006.01)
*G01N 33/569* (2006.01)

(52) U.S. Cl. .................. 435/7.1; 435/6; 435/320.1; 536/23.1

(58) Field of Classification Search ............. None
See application file for complete search history.

(56) References Cited

U.S. PATENT DOCUMENTS 5,667,973 A 9/1997 Fields et al.
5,695,937 A 12/1997 Kinzler et al.
5,866,330 A 2/1999 Kinzler et al.
2003/0143578 A1 7/2003 Pruitt et al.

OTHER PUBLICATIONS

Fields et al. A novel genetic system to detect protein-protein interactions. Nature 340: 245-246, 1989.*
White, M. The yeast two-hybrid system: Forward and reverse. PNAS 93: 10001-10002, 1996.*
Zhang et al., *Cre recombinase-mediated inversion using lox66 and lox71: method to introduce conditional point mutations into the CREB-binding protein*, Nucleic Acids Research, 2002, vol. 30, No. 17, e90, pp. 1-5.
Vidal, M et al., Yeast forward and reverse 'n'-hybrid systems. Nucleic Acids Research, Feb. 1999, vol. 27, No. 4, pp. 919-929.

* cited by examiner

*Primary Examiner*—David Guzo
*Assistant Examiner*—Michele K. Joike
(74) *Attorney, Agent, or Firm*—Hodgson Russ LLP

(57) ABSTRACT

The present invention provides a method for identifying a plurality of pairs of interacting proteins and plasmids for use in the method. The pair of plasmids is adapted for use in a modified two hybrid system wherein wherein each plasmid comprises a recombinase recognition site. The method comprises the steps of providing cDNAs encoding test polypeptides, inserting the cDNAs into the first and second plasmids, recombining the first and second plasmids to obtain recombined plasmids, isolating and digesting the recombined plasmids, ligating the restriction fragments to a universal adapter to provide a pool of digested fragments flanked by a universal adapter, selecting and amplifying desired sequences, forming concatamers from the amplified sequences, and sequencing the concatamers to determine the nucleotide sequences encoding a plurality of pairs of interacting proteins.

6 Claims, 8 Drawing Sheets

Fig. 1
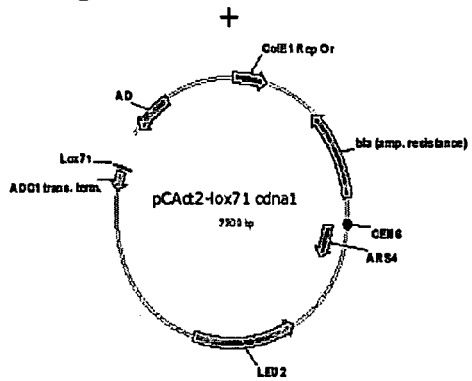
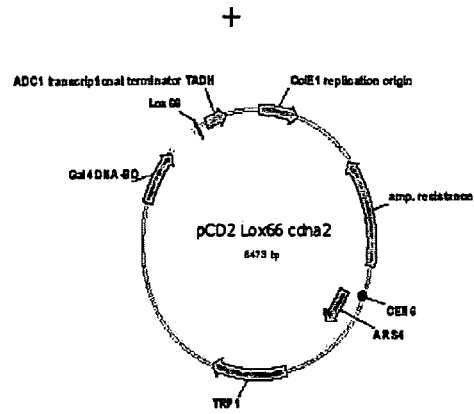
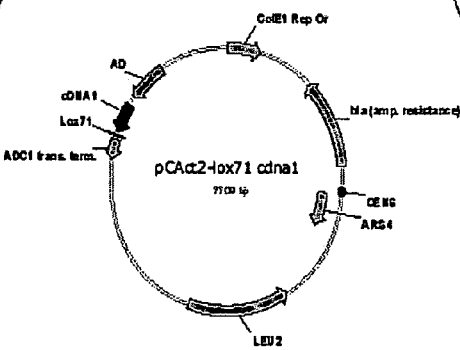
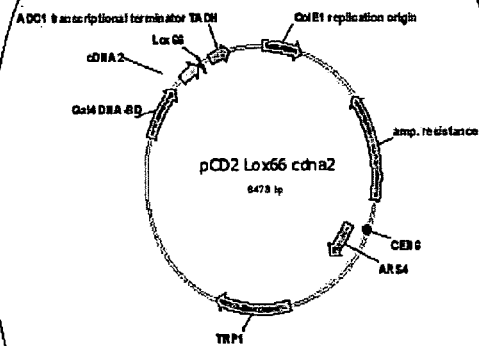
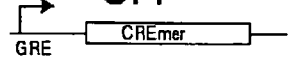
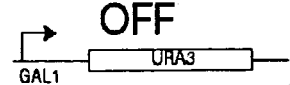

METHODS FOR PROTEIN INTERACTION DETERMINATION

This application claims the priority of U.S. Provisional Application Ser. No. 60/469,342, filed on May 9, 2003, the disclosure of which is incorporated herein by reference.

This invention was supported by grant number GM68856 from the National 0Institutes of Health. The Government has certain rights in the invention.

FIELD OF THE INVENTION

The present invention relates generally to the area of protein interactions and more particularly provides methods and compositions useful for rapid identification of protein interactions.

BACKGROUND OF THE INVENTION

It is widely recognized that binding between proteins is central to virtually all biological processes. With several completed genome sequences as a frame work with which to interpret such interactions, several large scale projects have attempted to define protein interactions for all of the open reading frames of simple organisms including viruses, bacteria, yeast, *Drosophila* and *C. elegans*.

Although other methods of defining protein interactions are possible, the most highly developed method for genome-wide analysis is the original yeast two-hybrid system in which interactions are monitored by the induction of gene expression. This technology can be used in a variety of cell types, including mammalian cells.

Two hybrid analysis works by separating the DNA binding domain (DBD) and activation domain (AD) of a transcriptional activator by cloning their respective coding sequences into separate vectors. One or both DBD and AD coding regions are then fused to many different open reading frames (ORFs), typically from a cDNA library. In the case where the two hybrid system is used in yeast, the DBD and AD vectors can be introduced into the same cell by mating and using DBD and AD vectors that each includes a selectable marker.

If the proteins expressed from the ORFs physically interact, the two halves of the transcriptional activator are brought together and the function of the transcriptional activator is restored. The reconstituted transcriptional activator can then drive expression of a selectable marker, such as a nutritional marker. When the reporter gene is detected, the plasmids with the interacting DBD and AD can be isolated from yeast colonies and the interacting ORF's identified by DNA sequencing.

Large scale projects to define all of the interactions occurring between all of the ~6,000 open reading frames in yeast have been accomplished using the yeast two hybrid system. However, application of this technology to mammalian genomes, which contain on the order of 10-fold greater complexity, is currently not feasible due to the exponentially greater number of potential interactions that must be scored. Thus, there is a need for an efficient method of identifying genome-wide protein interactions for organisms with complex protein interactions. The present invention meets this need by providing a modification of two-hybrid technology that permits the identification of many pairs of interacting proteins.

SUMMARY OF THE INVENTION

The present invention provides a method for identifying a plurality of pairs of interacting proteins and plasmids for use in the method.

The invention provides a plasmid pair adapted for use in a modified two hybrid system wherein first plasmid comprises a coding sequence for a DNA binding domain of a transcription activator (the "DBD plasmid") and the second plasmid comprises a coding sequence for a transcription activation domain of a transcription activator (the "AD plasmid"), and each plasmid further comprises a recombinase recognition site.

The method comprises the steps of providing cDNAs encoding test polypeptides, inserting the cDNAs into the first and second plasmids, recombining the first and second plasmids to obtain recombined plasmids, isolating and digesting the recombined plasmids, ligating the restriction fragments to a universal adapter to provide a pool of digested fragments flanked by a universal adapter, selecting and amplifying desired sequences, forming concatamers from the amplified sequences, and sequencing the concatamers to determine the nucleotide sequences encoding a plurality of pairs of interacting proteins.

BRIEF DESCRIPTION OF FIGURES

FIG. 1. is a graphical representation of one embodiment by which the generation of AD (left) and DBD (right) libraries in yeast by homologous recombination mediated gap repair can be achieved.

FIG. 3A is a graphical representation of pairs of linked, double stranded cDNAs are shown as they appear in the recombined plasmid. "A" and "a" in the hatched boxes represent the first pair and "B" and "b" represent the second pair of cDNAs. Also shown are the MmeI recognition site (closed circle), the MmeI cleavage site (arrow), and the recombined Lox66/71 sites.

FIG. 3B is a graphical representation of the products of MmeI digestion after ligation of universal adapters ("UA") comprising an XbaI restriction endonuclease.

FIG. 3C is a graphical representation of concatamers of XbaI digest fragments of the polynucleotides of FIG. 3B. cDNAs encoding interacting proteins flank lox sites and are separated from other pairs of interacting cDNAs by remaining adapter and XbaI sequences.

Figure 2:
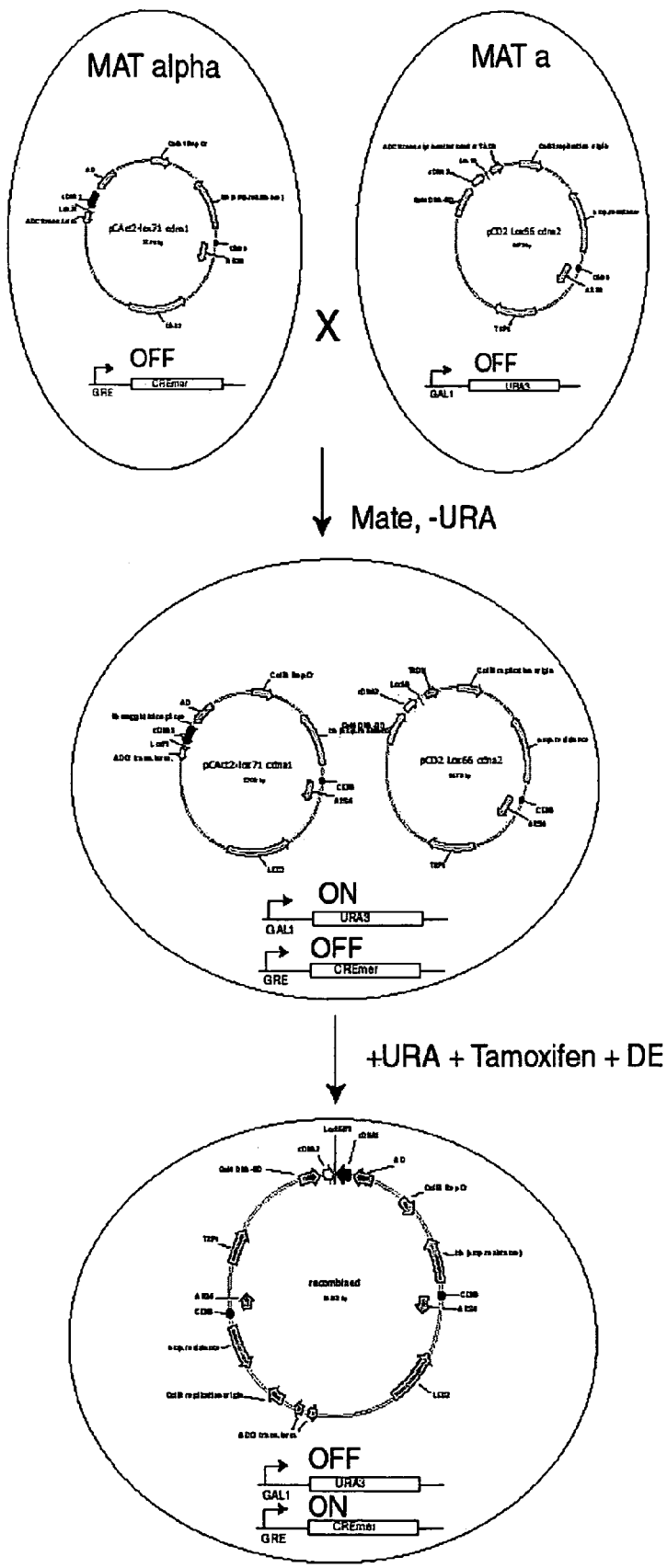
FIG. 2. is a graphical representation of one embodiment of a scheme for mating AD and DBD libraries. Schematics of the vectors (episomes) carried by the MAT-alpha-AD library (left) and MAT-a-DBD library (right) strains are shown as circles. A tamoxifen inducible Cre-recombinase gene, under the control of a DEX responsive element is present in the MAT-alpha strain is indicated as the boxed "CREmer". Both strains carry Ura3 and His3 under the control of UAS(G) where only the Ura3 gene is shown and is indicated as the boxed "URA3".

Lane 1 is 30 pg/ea of HindIII digested pGADT7lox71 and pCDlox66 this is to show the size of the unrecombined plasmids (carrots). Next to it is #2, is an empty lane, the marks are apparently some sort of artifact. #3 and #4 was meant to be a positive control using gene trap vectors, but since they did not come out cleanly; I cannot really tell if it worked. I

DETAILED DESCRIPTION OF THE INVENTION

The present invention provides compositions and methods for determining the identity of pairs of interacting proteins. In one embodiment, a method is provided for determining the identity of a plurality of pairs of interacting proteins. A "pair of interacting proteins" comprises a first test protein and a second test protein, wherein the first and second test proteins interact with each other in a cell.

Overall, the method of the present invention can be represented by the following steps.

a) providing a library of test cDNAs in which protein-protein interactions are to be determined;

b) providing a first and a second plasmid adapted for the modified two hybrid system, wherein the first plasmid comprises the coding region of a binding domain of a transcription activator (DBD plasmid) and the second plasmid comprises the coding region of a transcription activation domain for the transcription activator (AD plasmid), and wherein both plasmids have elements for homologous recombination with cDNAs encoding the first and second test proteins, promoters for driving transcription of the inserted cDNAs, drug selection, nutritional selection, origins of replication and recombinase recognition sites;

c) inserting the cDNAs into the first and a second plasmids such that each plasmid has one cDNA inserted therein thereby creating a library of inserted first and second plasmids;

d) obtaining recombed plasmids by i) introducing a pair of a first and a second inserted plasmids into host cells to obtain recombed plasmids in the host cells or ii) introducing the first inserted plasmid into a host cell and the second inserted plasmid into another host cell and allowing mating of the two host cells e) isolating and digesting the recombined plasmids to obtain from each recombined plasmid, a restriction fragment comprising a sequence from each of the two interacting proteins;

f) flanking each restriction fragment with a sequence for a universal adapter;

g) ligating the flanked restriction fragments to form concatamers, wherein the concatamers comprise from 5' to 3': universal adapter sequence, a first cDNA sequence encoding a first test protein, Type II S restriction enzyme recognition sequence, recombinase recognition sequence, Type II S restriction recognition sequence, and a second cDNA sequence encoding a second test protein, wherein the first and second cDNA sequences are from a single recombined plasmid; and h) sequencing the concatamers to determine the identity of interacting proteins.

Accordingly, the present invention provides a vector system and a method for establishing a comprehensive protein interaction map from a cDNA library by adapting two hybrid technologies to allow physical linkage of cDNAs encoding interacting proteins and to improve the efficiency of identifying interacting cDNA sequences by modifications allowing the application of a modified serial analysis of gene expression (MAGE). The elements for MAGE are described in U.S. patent application Ser. No. 10/227,719, filed on Aug. 26, 2002, which is incorporated herein by reference and is discussed more fully below. The modified two hybrid system of the present invention generates physically linked cDNAs which encode interacting proteins and which can be concatamerized for efficient analysis by MAGE. The advantage of this approach is that it is possible to identify many pairs of interacting proteins from a single mixed pool of yeast, or other cell types appropriate for the two-hybrid system used, in which multiple, different, protein-protein interactions are represented. Additionally, the data compression technique MAGE has been adapted in the present invention to allow improved efficiency in a cDNA sequencing step.

The method comprises the step of ligating a cDNA library into each of a first and second set of plasmids and transforming the plasmids into cells. Methods of ligating cDNA libraries into plasmids are well known to those skilled in the art. For example, the cDNAs and plasmids can be digested by a restriction enzyme and ligated in vitro. Alternatively, the cDNA library can be generated with specially adapted 5' and 3' ends for use in a yeast cell wherein the cDNA library and a linearized plasmid can be inserted into the yeast cell and joined together by the homologous recombination system of the yeast cell.

According to the method of the invention, the first plasmid comprises a coding sequence for a DNA binding domain of a transcription activator (the "DBD plasmid") and the second plasmid comprises a coding sequence for a transcription activation domain of a transcription activator (the "AD plasmid"), and each plasmid further comprises a recombinase recognition site. The DBD coding sequence is configured such that insertion of a cDNA into the DBD plasmid will result in the expression of a fusion of the DBD and a first test polypeptide encoded by the inserted cDNA. Similarly, the AD coding sequences are configured such that insertion of a cDNA into the AD plasmid will result in the expression of a fusion protein comprising the AD domain and a second test polypeptide encoded by the cDNA.

When a DBD and AD plasmid are in the same cell and their respective cDNAs encode test polypeptides that interact with each other, the interacting test polypeptides will bring into physical proximity their respective fused DBD and AD domains such that transcription of a selectable marker is driven from the promoter to which the DNA binding protein binds. In this way, cells having plasmid pairs comprising cDNAs that encode interacting test polypeptides can be selected for.

If cells comprising both the AD and DBD plasmids encoding interacting test polypeptides are present in the same cell, a recombinase acts to recombine the vectors at the recombinase recognition sites which results in the physical linkage of cDNAs encoding interacting test polypeptides.

The recombined plasmids can then be digested with a Type II S restriction enzyme, the resulting restriction fragments ligated to an adapter oligonucleotide to provide a pool of digested fragments flanked by the adapter, the fragments amplified by PCR, formed into concatamers and sequenced to determine the nucleotide sequences of cDNAs encoding pairs of interacting test polypeptides.

Plasmids

The present invention accordingly provides a plasmid system comprising AD and DBD plasmids. In addition to the activation domain on the AD plasmid and the DBD domain on the DBD plasmid, each plasmid comprises selectable markers such as antibiotic and/or nutritional markers, origins of replication, promoters, transcription terminators, a wild type or mutant recombinase recognition site, and cloning sites for insertion of cDNAs, as will be more fully described below.

Selectable markers for use in prokaryotic and eukaryotic systems are well known. For example, selectable markers for use in prokaryotes typically include genes conferring resistance to antibiotics such as ampicillin, kanomycin or tetracycline. For eukaryotes, neomycin (G418 or geneticin), gpt (mycophenolic acid), puromycin or hygromycin resistance genes are suitable examples of selectable markers. Genes encoding the gene product of auxotrophic markers (e.g., LEU2, URA3, HIS3, TRP1, ADE2, LYS2) are often used as selectable markers in yeast and are well known in the art. Further, dihydrofolate reductase marker genes permit selection with methotrexate in a variety of hosts.

Origins of replications included with the plasmids of the invention are considered to be sequences that enable the plasmids to replicate in one or more selected host cells independently of the host chromosomal DNA and include autonomously replicating sequences. Such sequences are well known for use in a variety of prokaryotes and eukaryotes. Examples of origins of replication for use in a plasmids in eukaryotic host cell include the 2 micron origin of replication, ARS 1, ARS4, the combination of ARS 1 and CEN3, and the combination of ARS4 and CEN6. Examples of origins of replication for use in plasmids in a prokaryotic cell include pBR322 and pUC.

Examples of promoters useful in practicing the present invention include any promoter that can drive the expression of a selectable marker. Preferable promoters are those that can be activated by a transcription activator comprising a DBD domain and a transcription AD, such as the VP16 or GAL4 promoters.

In one embodiment, an expression plasmid containing the AD or DBD domain is preferably a yeast vector such as pACT2 (Durfee et al., Genes Dev. 7, 555, 1993), pGADT7 ("Matchmaker Gal4 two hybrid system 3 and libraries user manual" 1999), Clontech PT3247-1, supplied by Clontech, Palo Alto, Calif.) or pCD2 (Mol. Cell. Biol., 3, 280 (1983), and plasmids derived from such yeast plasmids.

cDNA Libraries cDNAs for insertion into the vectors of the present invention are obtained by PCR amplification using well known techniques. In general, total RNA is isolated from cells according to well known methods and reverse transcriptase synthesized mRNA is generated using random priming for the first strand synthesis. Subsequent rounds of amplification are performed using standard PCR techniques.

In one embodiment of the invention, sequence fragments homologous to the sequences on the plasmid vector are added to the 5' and 3' ends of each cDNA in the RT-PCR and subsequent PCR amplifications. This can be achieved by using a pair of PCR primers that incorporate the added sequences. Any sequences can be added to the PCR primers according to those skilled in the art.

In one embodiment, SMARTIII and CDSIII primer sequences are modified to allow incorporation of a type II S restriction endonuclease cleavage site into the cDNAs. cDNA synthesis using the modified SMART primers can be performed with nanogram quantities of total RNA. The SMART system (i.e., see Clontech SMART PCR cDNA Library Construction Kit (July 1998) CLONTECHniques XIII(3):9-10) uses a modified random primer to prime synthesis of the first strand in a PCR reaction. When reverse transcriptase reaches the 5' end of the mRNA a few additional nucleotides, primarily deoxycytidine, are added to the 3' end of the cDNA.

SMART primers have an oligo(G) sequence at their 3' ends. This oligo(g) hybridizes with the 3' deoxycytidines, creating an extended PCR template. Reverse transcriptase (RT) then switches templates and continues replicating to the end of the oligonucleotide. The resulting single-stranded cDNA contains sequences that are complementary to the SMART primer. A SMART anchor sequence and the modified CDS primer derived sequences are then used as universal priming sites for end-to-end cDNA amplification by PCR. In one embodiment, long distance PCR ("LD-PCR") can be performed using standard techniques which allows amplification of longer sequences.

Inserting cDNAs cDNAs can be inserted into the vectors of the present invention using well known techniques. For example, the cDNAs and plasmids may be digested with restriction enzymes and ligated together in vitro.

Alternatively, the library of AD and DBA vectors of the present invention can be generated by exploiting the inherent ability of yeast cells to facilitate homologous recombination at a high efficiency. Yeasts such as *Saccharomyces cerevisiae* have inherent genetic machinery to carry out efficient homologous recombination. This mechanism is believed to benefit the yeast cells for chromosome repair purposes and is traditionally also called gap repair. By using homologous recombination in yeast, gene fragments such as cDNAs can be cloned into a plasmid vector without a ligation step. Accordingly, the linearized plasmids and the cDNAs are co-transformed into host cells, such as competent yeast cells. Recombinant clones may be selected based on survival of cells in a nutritional selection medium or based on other phenotypic markers. Either the linearized vector or the cDNA alone may be used as a control for determining the efficiency of recombination and transformation.

In one embodiment, the method comprises the step of transforming into a first set of yeast cells a library of cDNAs that are linear and double-stranded, and a first linearized plasmid, such as either the AD or DBD plasmid. Each of the cDNA sequences comprises a 5'- and 3'-flanking sequence at the ends of the cDNA sequence. The 5'- and 3'-flanking sequence of the cDNAs are sufficiently homologous to the 5'- and 3'-terminus sequences of the linearized plasmids to enable homologous recombination to occur. Using the same strategy, the linear and double-stranded cDNA sequences are transformed into a second set of yeast cells (either the AD or DBD) along with a second linearized plasmid.

Recombining the Plasmids by Cre-Mediated Linkaze of cDNAs Encoding Interacting Proteins In order to realize the potential of the present invention to identify many pairs of interacting proteins, it is necessary to recombine the first and second plasmids into a single plasmid. In one embodiment, the recombination was demonstrated by transfection of an AD plasmid and a DBD plasmid into a mammalian cell using standard techniques. Because the plasmids each comprise recombinase recognition sites, a recombinase is able to catalyze the recombination of the two plasmids into a recombined plasmid.

Any recombinase can be used for this purpose. A preferred recombinase is CRE recombinase. CRE is a 38-kDa product of the cre (cyclization recombination) gene of bacteriophage P1 and is a site-specific DNA recombinase of the Int family. CRE recognizes a 34-bp site on the P1 genome called loxP (locus of X-over of P1) and efficiently catalyzes reciprocal conservative DNA recombination between pairs of loxP sites. The loxP site consists of two 13-bp inverted repeats flanking an 8-bp nonpalindromic core region. CRE-mediated recombination between two directly repeated loxP sites results in excision of DNA between them as a covalently closed circle. Cre-mediated recombination between pairs of loxP sites in inverted orientation will result in inversion of the intervening DNA rather than excision. Breaking and joining of DNA is confined to discrete positions within the core region and proceeds on strand at a time by way of transient phophotyrosine DNA-protein linkage with the enzyme.

The CRE recombinase also recognizes a number of variant or mutant lox sites relative to the loxP sequence. Examples of these Cre recombination sites include, but are not limited to, the loxB, loxL and loxR sites which are found in the *E. coli* chromosome. Other variant lox sites include, but are not limited to, loxB, loxL, loxR, loxP3, loxP23, lox.DELTA.86, lox.DELTA.117, loxP511, and loxC2. In one embodiment of the invention, a pair of lox66 and lox71 sites can be used for in Cre-mediated recombination which results in mutant lox site resistant to recombination by Cre recombinase.

Examples of the non-CRE recombinases include, but are not limited to, site-specific recombinases include: att sites recognized by the Int recombinase of bacteriophage lambda. (e.g. att1, att2, att3, attp, attB, attL, and attR), the FRT sites recognized by FLP recombinase of the 2µ plasmid of *Saccharomyces cerevisiae*, the recombination sites recognized by the resolvase family, and the recombination site recognized by transposase of *Bacillus thruingiensis*.

To physically link cDNAs encoding interacting proteins within the cell, a coding region for the recombinase is provided in the genome of the cell. A preferable recombinase is tamoexfin inducible Cre named CreMer under the control of a DEX inducible promoter comprising glucocorticoid response elements. The glucocorticoid response elements allow induction of CreMer expression to high levels on treatment with DEX but show very low basal levels of expression in its absence. Additionally the CreMer variant of Cre requires the presence of tamoxifen for activity. This dual control allow tights regulation and permits a high degree of control over the expression of Cre activity. Thus, when a cell comprising a coding region for CreMer and the DBD and AD plasmids of the present invention, administering DEX and tamoxifen to the cell will induce expression of CreMer and cause recombination of the vectors.

In another embodiment, the DBD and AD vectors of the invention are each present in yeast cells of the opposite sex. Because yeast has two sexes (a and a), the DBD and AD vectors can easily be introduced into the same yeast cell by mating DBD and AD vectors that each include a selectable marker. Accordingly, in one embodiment of the invention, a yeast cells comprising a DBD plasmid is mated to a yeast cell comprising a AD plasmid. The plasmids can be maintained separately from each other by the use of selectable markers, such as by nutritional selection. Upon mating and activation of CreMer supplied for example from a CreMer gene endogenous to one of the yeast strains, the AD and DBD plasmids will be recombined at their lox sites such that the lox sites will be present in between the cDNAs of the first and the second fusion test proteins. The recombined plasmids can be selected for by requiring the AD and DBD proteins to interact by way of their fusion test polypeptides and drive the expression of yet another selectable marker, such as a nutritional selectable marker. The most commonly used yeast markers include URA3, HIS3, LEU2, TRP1 and LYS2, which complement specific auxotrophic mutations in yeast, such as ura3-52, his3-D1, leu2-D1, trp1-D1 and lys2-201.

Sequencing Recombined Vectors

A key to the ability of the present technology to provide a wide profile of protein-protein interactions is by permitting the efficient sequencing of cDNAs encoding the pairs of interacting proteins. This is accomplished using a modified version of the Serial Amplification of Gene Expression technology in a high throughput format. This technology is referred to as Modified SAGE technology (MAGE). Accordingly, the vectors comprises the elements for the modified serial analysis of gene expression (MAGE), (described in U.S. patent application Ser. No. 10/227,719, filed on Aug. 26, 2002, incorporated herein by reference).

MAGE is a high throughput method for the identification of DNA sequences. The method depends on the incorporation of type II S endonuclease restriction (such as BsgI, BpmI, or MmeI) recognition sequences adjacent to inserted cDNAs. These type II S restriction endonucleases have the property that each cleaves DNA at a position 16, 20 or 21 nucleotides adjacent to its recognition sequence where the composition of the adjacent nucleotides is irrelevant. Using the example of BsgI and MmeI, the present invention takes advantage of this property to allow the amplification of up to 21 nucleotides of the cDNA sequence adjacent to the cDNA insertion site.

Following this, bits of unknown sequence information referred to as "sequence tags" can be identified because these are separated by repeats of a known sequence. In the present application, this is accomplished by ligating the PCR products with the aid of a restriction endonuclease cleavage site present in both the universal primer and adjacent vector sequence. The ligated strings of sequence tags are then cloned and sequenced. Thus, sequence tags representing pairs of interacting proteins can be identified from the sequences generated from the ligated PCR products.

Figure 3:
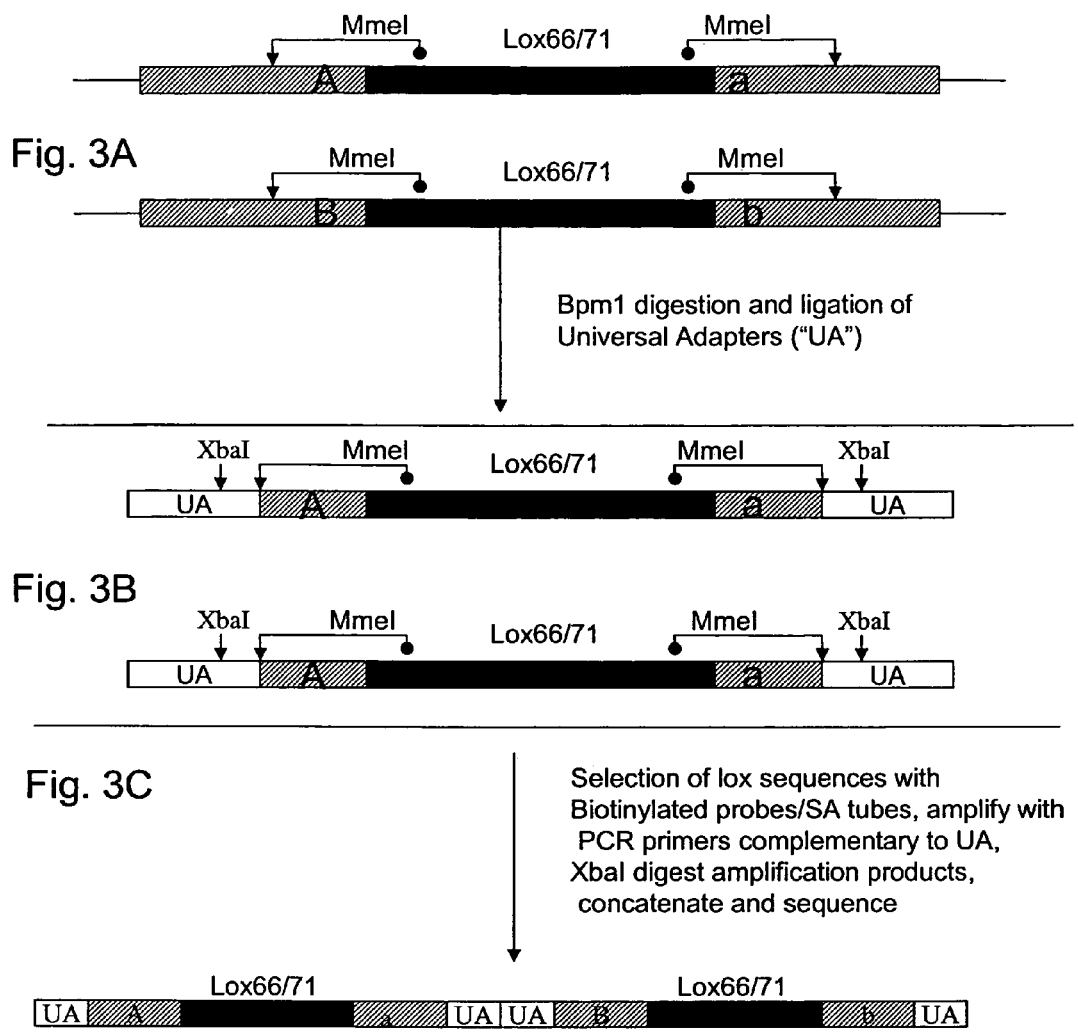
FIG. 3A-C. are a graphical depiction of recovery of linked cDNAs and compression of the sequence data that is identified through a modification of the MAGE technology.

An illustrative overview of one embodiment of the invention utilizing yeast is shown in FIGS. 1-3. FIG. 1 illustrates the construction of the activation domain AD and binding domain DBD libraries in MAT-alpha and MAT-a strains of yeast. FIG. 2 illustrates mating of these strains and one embodiment for selection of interacting proteins by induction of recombination between plasmids comprising cDNAs encoding the interacting proteins. FIG. 2 shows graphical representations of particular embodiments of the plasmids carried by the MAT-alpha-AD library (left) and MAT-a-DBD library (right) shown as circles. A tamoxifen inducible Cre-recombinase gene under the control of a DEX responsive element is present in the MAT-alpha strain as indicated. Both strains carry Ura3 and His3 under the control of UAS(G) where only the Ura3 gene is shown. Strains are mated and selected for activation of the Ura3 and His1 genes mediated by two-hybrid interactions using SD-URA, -HIS dropout media. Following selection, physical linkage of the cDNAs encoding the interacting proteins may be accomplished by inducing CreMer expression with DEX and addition of tamoxifen. The orientation of the vector sequence can enable resolution of the recombined molecules, leaving the fused cDNAs on plasmid carrying the bacterial ori sequence, ampicilin resistance gene, a single centromeric sequence and either Trp or Leu (not shown). Recombination between the cDNAs will (or should) result in loss of Ura3 and His3 expression mediated by the interacting proteins. Selection for cells in which this has occurred is possible by growth on 5-FOA (not shown).

FIGS. 3A-C illustrate recovery of the linked cDNAs and compression of the sequence data with a modification of the MAGE technology. In FIG. 3A two pairs of linked, double stranded cDNAs are shown as they appear in the recombined plasmids. "A" and "a" in the hatched boxes represent the first pair and "B" and "b" represent the second pair of cDNAs. Also shown are the MmeI recognition site (closed circle), the BpmI cleavage site (arrow), and the recombined Lox66/71 sites.

FIG. 3B depicts the products of MmeI digestion after ligation of universal adapters ("UA") comprising an XbaI restriction endonuclease. The cDNAs to be detected can be selected for in streptavadin (SA) tubes with biotinylated oligonucleotides that are complementary to the recombined lox sequences (not shown). The fragments depicted in FIG. 3B are amplified by PCR using primers complementary to the UA sequences. The amplification products are digested with XbaI and ligated together to form concatamers as shown in FIG. 3C.

As can be seen from in FIG. 3C, the cDNAs encoding interacting proteins can be determined because each cDNA of a pair is separated from its mate by an intervening lox sequence, and each pair of cDNAs is separated from other pairs by the UA sequence remaining after XbaI digestion.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

EXAMPLE 1

This embodiment demonstrates the construction of a pair of plasmids useful for practicing the present invention in yeast. In this embodiment, the starting point for construction of the AD and DBD vectors were pCAct2 (AD vector) and pCD2 (DBD vector), which were obtained through the American Type Culture Collection (ATCC). These vectors are low copy number and contain CEN6 sequence elements. In this embodiment, two modifications to these vectors were made to prepare them for Cre mediated recombination to physically link the cDNAs they carry.

First, a region of pCAct2 carrying the ADC1 promoter, AD, site of cDNA insertion and transcription termination site is inverted relative to the remaining vector sequences. This is required to allow resolution of recombined plasmids in the final step of the selection as will be described more fully below. Second, lox sequences are inserted in both pCAct2 and pCD2. In this embodiment, pCAct2 received the half site mutant lox71 and pCD2 received the half site mutant lox66. Recombination between these lox sites generated a defective lox66/71 element that is no longer able to mediate efficient recombination and locks in the fusion between the cDNAs even in the continued presence of Cre.

Figure 5A:
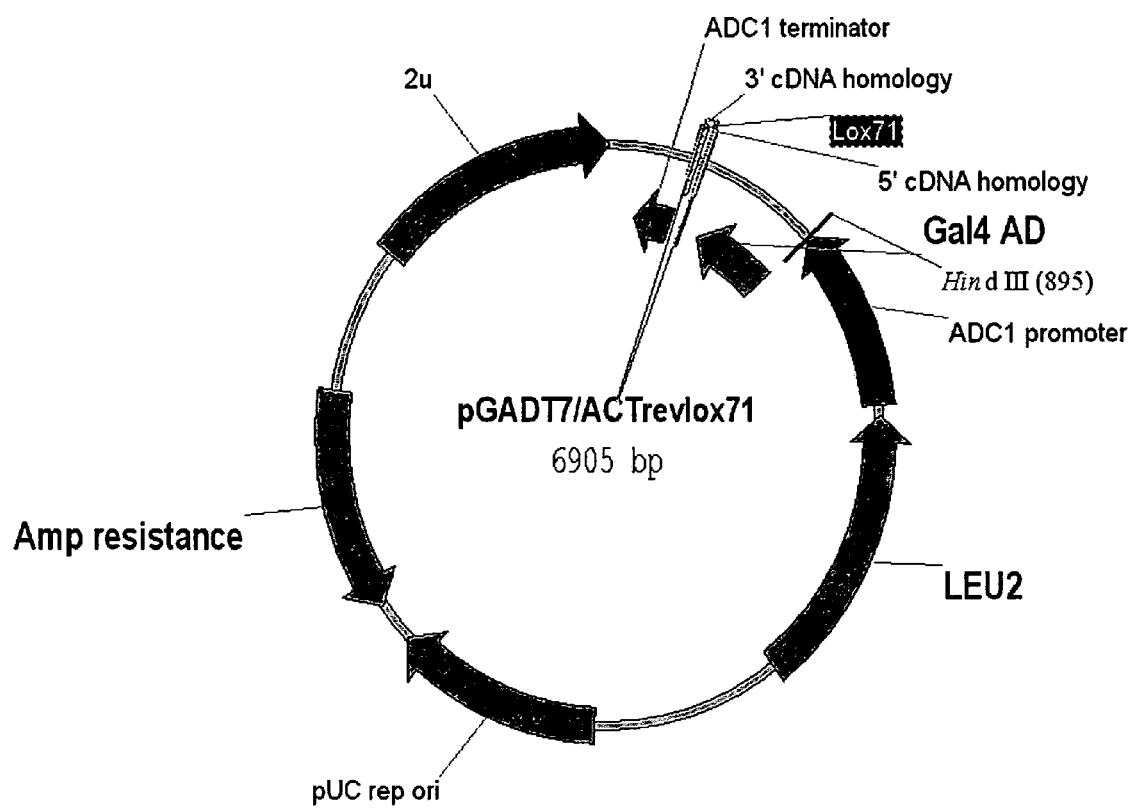
FIG. 5A. is a graphical representation of a high copy number 2μ based two-hybrid AD fusion vector with lox71 sequence integrated adjacent the 3' cDNA cloning site. Also shown are various selectable markers and "3' cDNA homology" and "5' cDNA homology" sites for homologous with cDNAs.
Figure 5B:
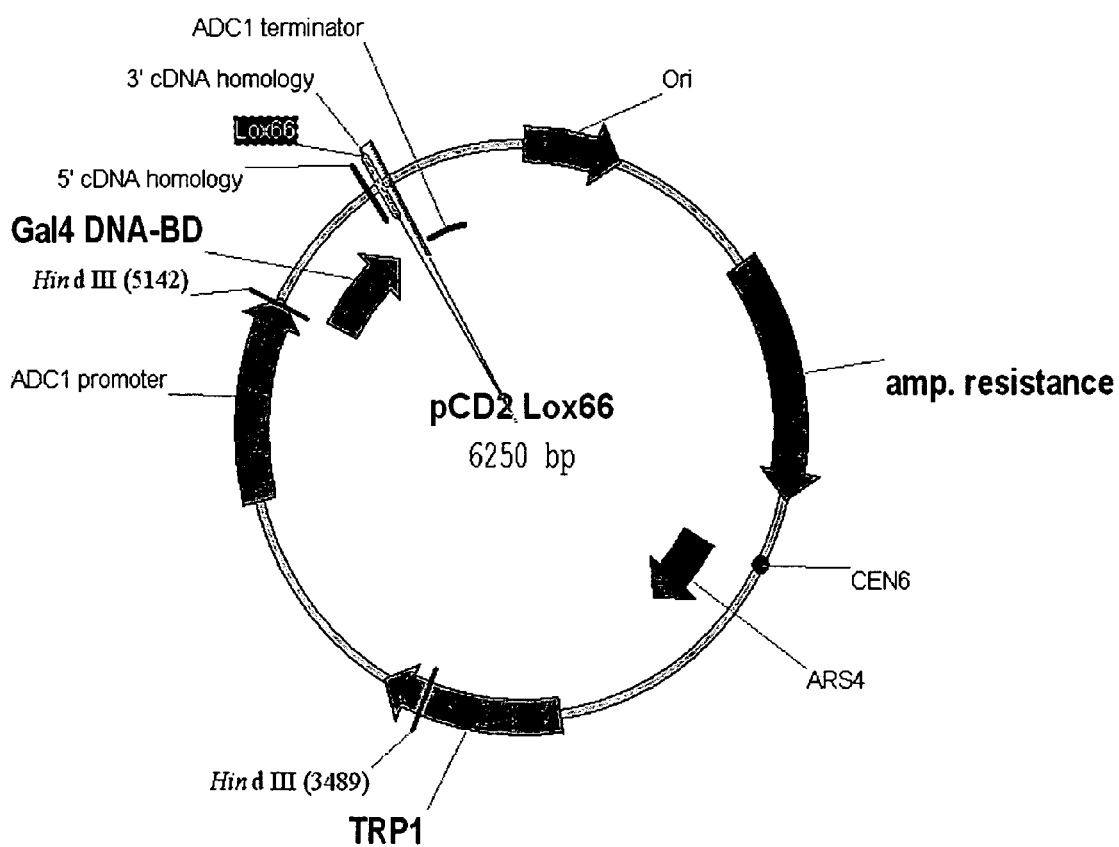
FIG. 5B is a graphical representation of a low copy number CEN based two-hybrid DBD fusion vector with lox66 sequence integrated adjacent the 3' cDNA cloning site with additional features as described for FIG. 5A.
Figure 5C:
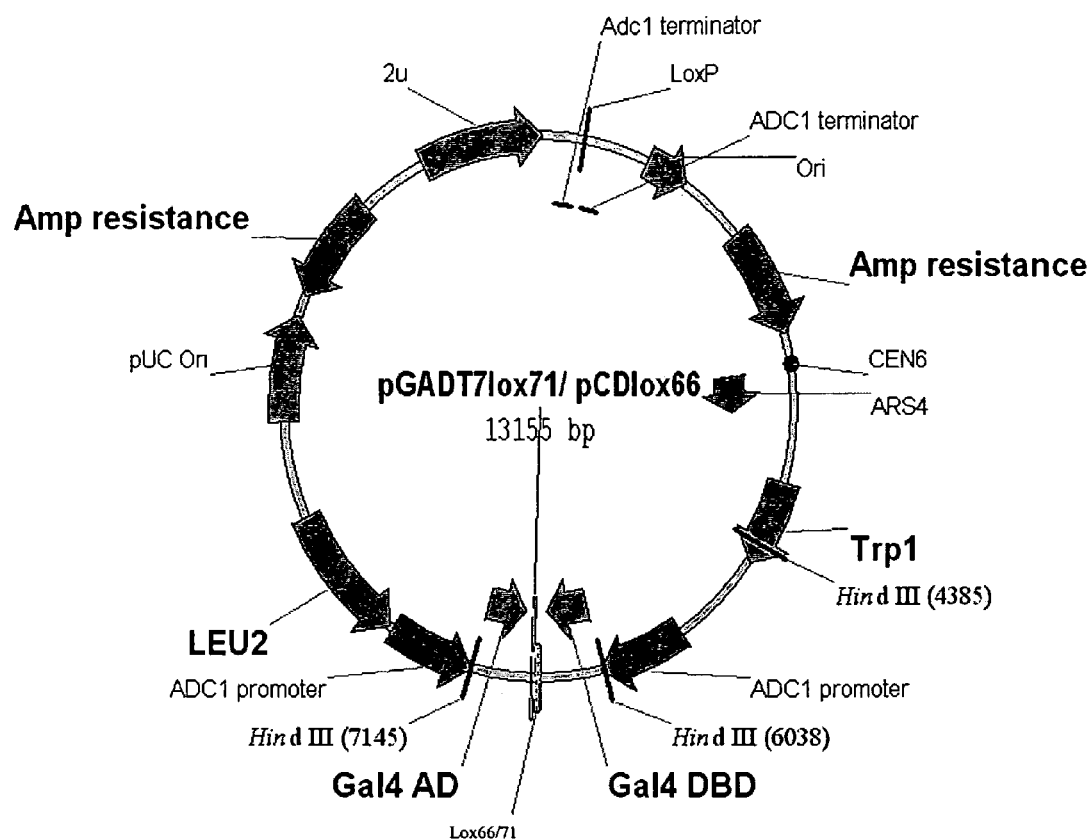
FIG. 5C is a graphical representation of one embodiment of a product of a stable site directed recombination between the AD and DBD plasmids resulting in cDNA cloning sites directly adjacent the doubly mutated lox66/71 sequence.

In another embodiment, a set of plasmids was also constructed that includes a high copy number 2 μm origin of replication. Shown in FIG. 5A is the pGADT7/ACTrevlox 71 plasmid which was constructed by removing the promoter, AD (or DBD), the cloning site, and the terminator from pGADT7rec and pGBKT7 (clontech) and replacing them with the ADC1 promoter, AD or BDB (as in FIG. 5B), the site of cDNA insertion, the lox71 sequence (or lox66 as in FIG. 5B) and transcription termination site from the CEN based plasmids described above.

EXAMPLE 2

This Example discloses one embodiment for the synthesis and incorporation of cDNAs into the AD and DBD plasmids described above by co-transfection of cDNAs containing the SMARTIII and CDSIII sequences with the AD and DBD plasmids.

Figure 4:
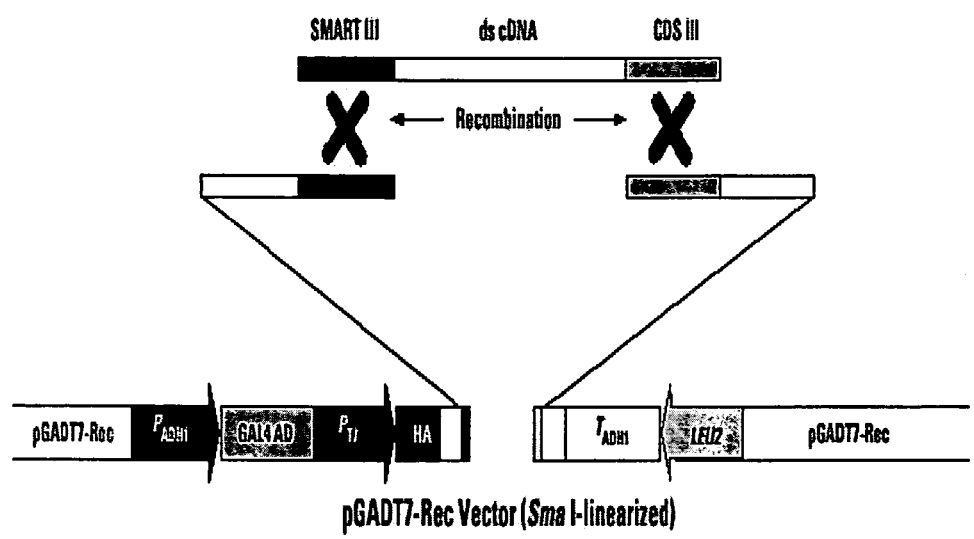
FIG. 4. A cloning vector (ClonTech pGADT7-Rec) and a representation of one embodiment of a cDNA library construction strategy is shown wherein cDNAs are prepared containing termini that are homologous to the insertion site in the vector and the vector introduced to yeast as a linear molecule in combination with the cDNAs for ligation by homologous recombination. This results insertion of a type II S restriction endonuclease cleavage site sequence element at the fusion point between the activation domain and the cDNAs by modifying the CDS III oligonucleotide to include the Type II S restriction enzyme.

Outlined in FIG. 4 is the ClonTech® pGADT7-Rec vector and cloning strategy used in one embodiment of the invention. cDNAs were prepared containing termini that are homologous to the vector's insertion site and the yeast were transformed with linearized vector in combination with the cDNAs. Subsequent recombination at the homologous sequences generated the desired fusions and the re-circularization of the vector allows growth in yeast. This approach allows insertion of the BpmI, or MmeI, site needed subsequently for MAGE (as explained below) and requires only that the 3' oligo sequence (equivalent to CDS III oligo shown in FIG. 4) is modified to include the BpmI, or MmeI, recognition sequences adjacent to the cDNA. The vector's homologous sequences are also modified to reflect those in the AD and DBD vectors described above.

In one embodiment, the primer sequences are:

```
pAct2 lox71 MAGE/6 Primer:
                                          (SEQ ID NO:1)
5'-GTATAGCATACATTATACGAACGGTAACCCTCTGAGCTGGAG-
                                    Xba I  Bpm I
NNNNNN-3'

PCD2 lox66 MAGE/6 Primer:
                                          (SEQ ID NO:2)
5'-CGTATAATGTATGCTATACGAACGGTACCCTCTGAGCTGGAG-
                                    Xba I  Bpm I
NNNNNN-3'
```

The Bpm I and Xba I sites are shown in bold. The 6 random nucleotides (N) are used to prime first strand cDNA synthesis and in many cases accurately represent the cDNA sequence.

In another embodiment, the primer sequences are:

```
Lox71 MmeI:
                                          (SEQ ID NO:3)
5'-TATAATGTATGCTATACGAACGGTAGGATCCAACNNNNNN-3'
                                      MmeI

Lox66 MmeI:
                                          (SEQ ID NO:4)
5'-CATATCGTATGTAATATGCTTGCCATAGGTTGNNNNNN-3'
                                  MmeI
```

The Mme I sites are shown in bold. The 6 random nucleotides (N) are used to prime first strand cDNA synthesis and in nearly all cases accurately represent the cDNA sequence.

Prior to cloning the cDNAs the cDNAs were normalized. The concentration of any specific message in the total population may vary over 3 to 4 orders of magnitude, hence the probability of finding interactions between two rare sequences would be low in the absence of a normalization step. A variety of methods have been described by which cDNAs can be normalized and any of these methods can be used in the present invention. In this embodiment, the normalization step was done by hybridization of cDNA to biotinylated driver cDNA, followed by removal of driver and abundant cDNA by streptavidin binding and phenol extraction. After normalization, the cDNAs were transfected into cells in conjunction with linearized AB and DBD plasmids to facilitate homologous recombination between the cDNAs and the plasmids.

The transformation efficiency of yeast using homologous recombination mediated gap repair is greater than 300,000 colonies per μg of starting vector. This efficiency is ample to allow generation of comprehensive cDNA libraries containing greater than 100,000 colonies. In this embodiment, the strains of yeast utilized take advantage of Ura3 selection from a Gal1 promoter to detect protein interactions. Ura3 expression can also be optionally counter-selected by the use of 5-fluoro-orotic acid (5-FOA, Boeke et al., 1984) which allows elimination of fusion proteins that auto-activate the Gal1 promoter in the absence of a dimerizing partner. Although a generally useful range of 5-FOA concentrations can be estimated from prior studies, titration of the concentration of 5-FOA against an aliquot of the transformed cells was performed where approximately 10,000 transformants were plated to a single 15 cm plate for each concentration in SD-URA media which also lacks either TRP or LEU depending on the vector. The same 5-FOA concentrations was used in parallel to test the effect on host cells in media containing URA, TRP and LEU. A concentration that has the maximum effect on suppressing growth of colonies from the cDNA libraries but minimal effect on the host cell was chosen for the remaining steps.

EXAMPLE 3

This example describes yeast cells having an endogenous CreMer gene for use with the present invention. The starting strains used for generating the CreMer expressing yeast strain were YD116 and YD119. These strains are both (ura3-52 his3-200 leu2-trp1-901 can(R) gal4delta512 gal80delta338 lys2-801::UAS(G)-HIS3-lacZ ade2-101:: GAL1-URA3) where YD116 is MAT-alpha and YD119 is MAT-a. To modify them for inducible Cre expression a tamoxifen inducible Cre variant (CreMer; Zhang et al., 1996) was inserted under the control of DEX inducible glucocorticoid response elements (Picard et al., 1990). This was accomplished by PCR based gene targeting using the pFA6a-kanMX6 module (Bahler et al., 1998) and selection in G418. Correct integration was confirmed by PCR. The glucocorticoid response elements allowed induction to high levels on treatment with DEX but show very low basal levels of expression in its absence. Additionally the CreMer variant of Cre requires the presence of tamoxifen for activity. This dual control allow tights regulation and permits a high degree of control over the expression of Cre activity. A strain of yeast of a particular sex harboring the CreMer gene and either a DBD or AD plasmid of the invention can be mated to a yeast of the opposite sex which harbors the complementary DBD or AD plasmid. In this way, activation of CreMer will catalyze recombination of the plasmids for sequencing analysis using the method of the present invention.

EXAMPLE 4

This Example demonstrates the mating of yeast cells wherein the opposite sexed cells harbor either DBD or AD plasmid such that mating the cells will provide cells with both DBD and AD plasmids. A comprehensive test of all interactions between the ~100,000 cDNAs carried in the libraries generated above requires that $1 \times 10^{10}$ diploid cells are generated. Optimized interaction-mating protocols have been developed that routinely allow mating efficiencies of 10% or greater (Soellick and Uhrig, 2001). These conditions are utilized here and require a low pH incubation of approximately $1 \times 10^8$ cells/ml followed by seeding the cells to a filter at a density of $2 \times 10^7$ cells/cm$^2$. Filters are transferred to agar and mating is allowed to occur for 4.5 hours prior to transfer to selection conditions. This protocol results in approximately $2 \times 10^6$ zygotes/cm$^2$ of filter area. To achieve $1 \times 10^{10}$ diploid cells requires the equivalent of 5,000 cm$^2$ of mating surface. Because a 15-cm filter allows approximately 176 cm$^2$ of surface, it is necessary to prepare approximately 30 such filters. Following mating, cells are removed from filters and pooled. Small aliquots are plated to SD-Leu, SD-Trp, SD-Leu-Trp to monitor the viability and mating efficiency. The remaining cells are plated to 15 cm plates in SD-Leu-Trp-Ura-His to select for interacting proteins. Based on an estimate of 300,000 potential interactions, each of 30 plates contain about 10,000 colonies, but the actual number of colonies is estimated and colonies are pooled.

EXAMPLE 5

Figure 5D:
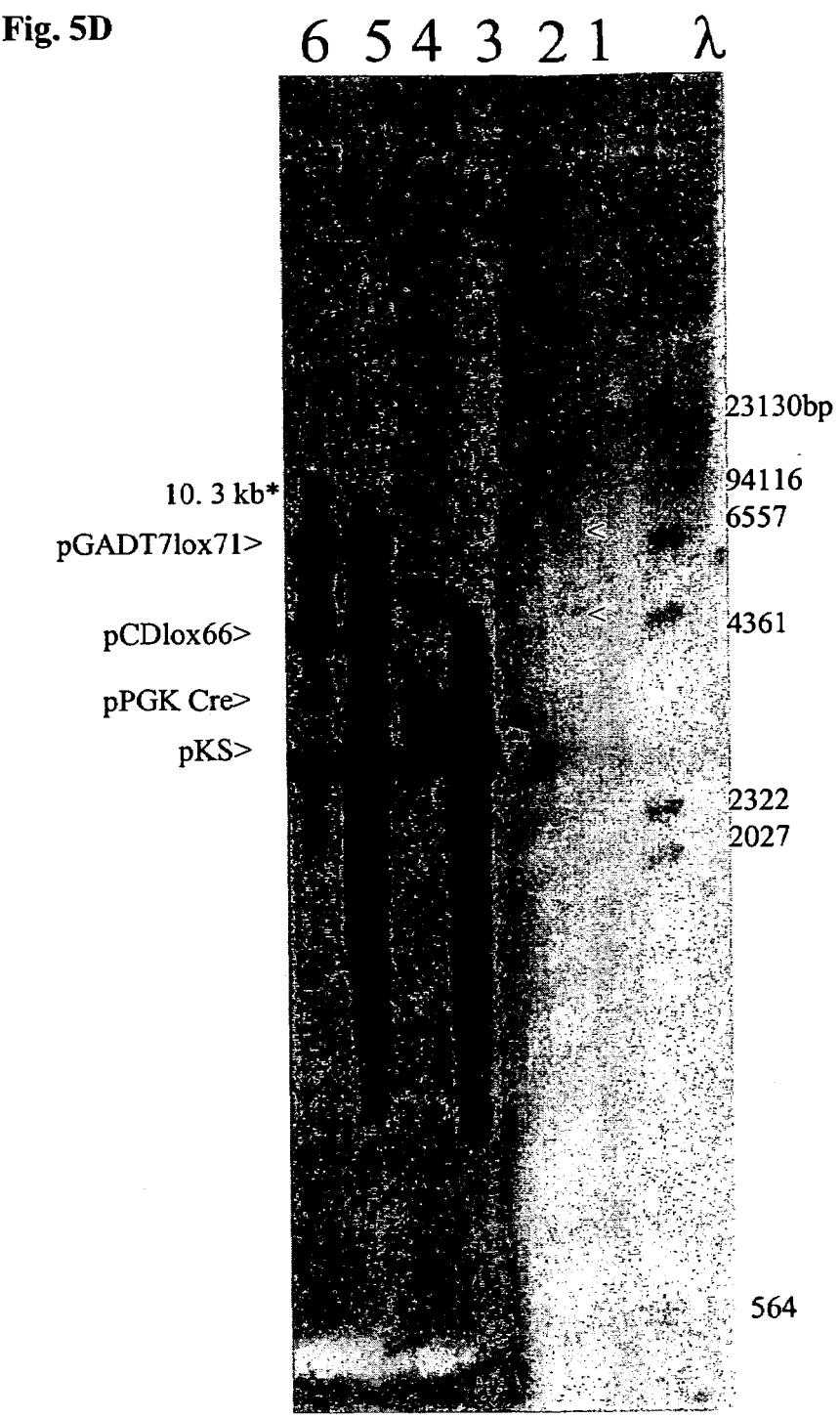
FIG. 5D is a representation of a Southern blot demonstrating in vivo Cre dependant recombination between lox66 and lox71 sequences adjacent the 3' cDNA cloning site of Gal4 DNA binding domain (DBD) and Gal4 activation domain (AD) Y2H vectors. The figure represents a Southern blot probed with a fragment of the ampicillin resistance gene. Lane λ is a size ladder, Lane 1 is empty, Lane 2 is each plasmid digested by HindIII (carrots). Lanes 3 and 4 are controls, Lanes 5 and 6 are DNA harvested from HEK 293 cells digested by HindIII that were transfected with 8 mg each of pBluescript and the two Y2H vectors depcited in FIGS. 5A and 5B (lane 5) and pPGKcre and the two Y2H vectors (lane 6). The band denoted by an asterisk is the product of Cre recombination that includes the ampicillin resistance gene.

This Example demonstrates that the plasmids of the present invention can be combined in vivo. As shown in FIG. 5D, transient transfection of the AB and DBD plasmids using standard techniques into HEK 293 cells depicted in FIGS. 5A and 5B above results in recombination of the plasmids.

FIG. 5D represents Cre dependant targeted recombination between lox66 and lox71 sequences adjacent the 3' cDNA cloning site of Gal4 DNA binding domain (in the DBD plasmid) and Gal4 activation domain (in the AD plasmid) in vivo. Depicted is as Southern blot probed with a fragment of the ampicillin resistance gene. Lane 1 is empty, Lane 2 shows the two plasmids digested by HindIII (carrots). Lanes 3 and 4 are control reactions, and Lanes 5 and 6 show DNA harvested from HEK 293 cells. The cells were transfected with 8 mg each of pBluescript as a control and two plasmid vectors of the present invention (lane 5) and pPGKcre and the two Y2H vectors (lane 6). The DNA was isolated and digested by HindIII. The band denoted by an asterisk is the product of Cre recombination that includes the ampicillin resistance gene. This Example therefore demonstrates that the plasmids of the present invention are able to undergo Cre-mediated recombination in vivo.

EXAMPLE 6

This Example demonstrates how Cre-mediated linkage of cDNAs encoding interacting proteins can be performed within a yeast cell where the interaction is occurring. Approximately $1\times10^9$ yeast cells in a total of 100 ml ($1\times10^7$ cells/ml) of the selected diploid cells can be inoculated to a liquid culture containing tamoxifen and DEX. In the absence of recombination, transcription of the Ura3 gene will continue because of the interaction of the AD and DBD cDNA fusion proteins at the Ura3 promoter. Ura, His, Trp and Leu may be present in this culture because recombination at the lox sites is expected to prevent expression of the fused cDNAs and resolution of the fusion plasmids through homologous recombination may lead to loss of either Trp or Leu resistance. Because the vectors used to construct the AD and DBD libraries carry a centromere and are low copy number, or in a situation where one or the other of the AD or DBD libraries carries a centromere and is present in low copy number, it may be useful to add FOA to the culture following sufficient time for Cre mediated recombination and the degradation of URA3 protein. This allows selection for cells in which lox sites have been recombined because, in the absence of recombination, transcription of the Ura3 gene will continue because of the interaction of the AD and DBD cDNA fusion proteins at the Ura3 promoter. The time required for efficient recombination and loss of URA3 activity can be determined empirically.

EXAMPLE 7

This Example illustrates a strategy by which recombined plasmids (episomes) can be recovered and linked cDNAs prepared for sequencing using the MAGE technique. Episomes, a portion of which comprising linked cDNAs A and a and B and b in the hatched boxes are as shown in FIG. 3A. These are recovered from yeast by standard techniques and used in a modified version of MAGE to extract sequence tag information from linked cDNAs. Linked sequence tags are referred to dimer-tags. Shown in FIG. 3B is the region of two episomes as prepared for linkage into a pool of linked cDNAs by ligation of a universal adapter (UA) which incorporates a restriction site (XbaI) into each MmeI fragment. Subsequent digestion with XbaI and concatamerization of the fragments results in linked pairs separated from each other by the lox66/71 sequence as shown in FIG. 3C.

To select specifically for the fragments containing the desired linked cDNA sequences, the intervening lox site is used as a hybridization probe. The ligation products are denatured and annealed to a 3' biotinylated oligonucleotide homologous to this sequence. Use of a 3' biotinylated probe prevents its participation in subsequent polymerization reactions. Hybrids are selected on streptavidin coated PCR tubes wherein the 3' biotinylated oligonucleotide complementary to the lox sites hybridizes to the lox sites flanked by the cDNAs and thereby retains the cDNAs in the PCR tubes. Washing removes the large majority of contaminating sequences and following the wash step, oligonucleotides homologous to the top strand of the adapter sequence are used as PCR primers. PCR reaction products are digested with Not I for which there is a cleavage site present in adapter sequence. Each fragment results in a fragment containing the dimer-tag and 2×21 nucleotide long adapter fragments. These are electrophoresed on an acrylamide gel, the 86 bp long fragment is recovered, ligated into concatamers and cloned into bacteria for sequencing. Any residual contaminating cDNA sequences that were not eliminated by the hybridization selection step will be further reduced in the population by size selection and are only a very minor contaminant, and such contaminants are easily recognized during sequencing.

A BD FACS-Vantage® with individual cell deposition capability is used to seed bacteria to microtiter wells for cloning. Standard high-throughput techniques are used to prepare plasmids for sequencing using protocols specific to suitable sequencing machines, such as Beckman® CEQ or Amersham® MegaBase 1000 capillary sequencers. Each sequence results in approximately 500-600 nt of useful sequence. Because each dimer-tag was 86 nucleotides in length, it was possible to identify an average of 5 interacting protein pairs from each sequence. This provides for cost-effective and comprehensive screening of protein interactions.

EXAMPLE 8

This Example demonstrates sequence tag analysis of cDNAs encoding AD test polypeptides that interact with Brn2 fused to the DBD of Gal4. These results were generated in yeast cells using DBD and AD plasmids wherein the AD cDNA library was created from poly A selected RNA from 9.5 day past coitus mouse embryos and in which a BpmI restriction enzyme site was incorporated adjacent the 3' end of cDNA during synthesis.

Table 1 represents concatamers that were cloned and sequenced (tags are underlined, linker sequence is italicized, cloning vector sequence is bold). Table 2 represents the deconvoluted sequence tags from the SEQ ID NO:5 in Table 1, and Table 3 represents results from a BLAST search conducted on the identified sequence tags and representative cDNA GenBank accession numbers for the isolated cDNAs.

TABLE 1

ATCCCCCGGGCTGCAGGAATTCGA TGCGATAATAACCACGGC *ACCACTGGAG*     (SEQ ID NO:5)

GGATCCCTTGATCAGA *CACCACTGGAG* CACGAGAAGAAGGAG *CCACCACTGGAG*

CACGAGAAGAAGGAGCT *CACCACTGGAG* GGATCCCTTGATCAGA *CACCACTGGA*

GGGGGTCGGGACGGAGA *CACCACTGGA* GGAGGGCACAGCAGAAG *CACCACTGGA*

GGGTGGGGACTTTCTCC *CACCACTGGA* GGGATCCCTTGATCATA *CACCACTGGAG*

AGGGTCCCGATGCTGG *CACCACTGGAG* CCTCGATCAGATCTGC *CACCACTGGAGC*

ACTAGAAAAAGAGGA *CACCACTGGA* GGAGGGCACAGCAGAAG *CACCACTGGAGG*

GTGGGGACTTTCNTCC *CACCACTGGAG* TGCTCGTTAGAATATT *CACCACTGGAGG*

GATCCCTTGATCANA *CACNTNCTGGAG* CGGACAGAGGANACNT *CNACCACTGGAG*

CGGCAGGGGAACTTAN *CCCCACTT* GGGACCACNANAAGNA

TABLE 2

| 1.  | CGATAATAACCACGGC  | (SEQ ID NO:6)  |
|---|---|---|
| 2.  | GGATCCCTTGATCAGA  | (SEQ ID NO:7)  |
| 3.  | CACGAGAAGAAGGAGC  | (SEQ ID NO:8)  |
| 4.  | CACGAGAAGAAGGAGCT | (SEQ ID NO:9)  |
| 5.  | GGATCCCTTGATCAGA  | (SEQ ID NO:10) |
| 6.  | GGGGTCGGGACGGAGA  | (SEQ ID NO:11) |
| 7.  | GAGGGCACAGCAGAAG  | (SEQ ID NO:12) |
| 8.  | GGTGGGGACTTTCTCC  | (SEQ ID NO:13) |
| 9.  | GGATCCCTTGATCATA  | (SEQ ID NO:14) |
| 10. | AGGGTCCCGATGCTGG  | (SEQ ID NO:15) |
| 11. | CCTCGATCAGATCTGC  | (SEQ ID NO:16) |
| 12. | CACTAGAAAAAGAGGA  | (SEQ ID NO:17) |
| 13. | GAGGGCACAGCAGAAG  | (SEQ ID NO:18) |
| 14. | GGTGGGGACTTTCNTCC | (SEQ ID NO:19) |
| 15. | TGCTCGTTAGAATATT  | (SEQ ID NO:20) |
| 16. | GGATCCCTTGATCANA  | (SEQ ID NO:21) |
| 17. | CGGACAGAGGANACNT  | (SEQ ID NO:22) |
| 18. | CGGCAGGGGAACTTAN  | (SEQ ID NO:23) |

TABLE 3

| AGGGTCCCGATGCTGG | (SEQ ID NO:15) |
|---|---|
| gi|38084558|ref|XM_132640.2| | |
| *Mus musculus* empty spiracles homolog 1 (Drosophila) (Emx1), mRNA | |
| GAGGGCACAGCAGAAG | (SEQ ID NO:12) |
| gi|25058121|gb|BC039041.1| | |
| *Mus musculus* zinc finger protein 326, mRNA | |
| GCAGATCTGATCGAGG | (SEQ ID NO:24) |
| gi|34447123|dbj|AB114630.1| | |
| *Mus musculus* CNR gene for cadherin-related neuronal receptor | |

This Example therefore illustrates the ability of the method of the present invention to identify multiple cDNAs encoding proteins that interact to drive expression of a reporter gene.

---

What is claimed is:

1. A method for identifying a plurality of pairs of interacting proteins wherein a pair of interacting proteins comprises a first test protein and a second test protein, wherein the first and second test proteins interact with each other in a cell, the method comprising the steps of:
   a) providing a cDNA library;
   b) providing a plurality of a first plasmid comprising a coding sequence for a DNA binding domain of a transcription activator, a first recombinase recognition site, a first selectable marker, a first Type II S restriction site and a first inserted cDNA encoding a first test protein;
   c) providing a plurality of a second plasmid comprising a coding sequence for a transcription activation domain of the transcription activator, a second recombinase recognition site, a second selectable marker and a second Type II S restriction site, and a second inserted cDNA encoding a second test protein, wherein the first and second recombinase recognition sites may be identical or distinct and the first and second Type II S restriction sites may be identical or distinct;
   d) introducing the first and second plasmids from b) and c) into the same cell;
   e) inducing the expression of the recombinase to recombine the first and second introduced plasmids;
   f) isolating and digesting the recombined plasmids with a Type II S restriction enzyme to obtain restriction fragments and ligating the restriction fragments to a universal adapter to provide a pool of digested fragments flanked by universal adapter sequences;
   g) forming concatamers from the pool of digested fragments and sequencing the concatamers to determine the identity of the plurality of pairs of interacting proteins.

2. The method of claim 1, wherein the first and second inserted cDNAs of steps b) and c) were inserted by homologously recombining the first and second cDNAs with the first and second plasmids, respectively.

3. The method of claim 1, wherein the Type II S restriction site is selected from the group consisting of BsgI, BpmI, and MmeI sites.

4. The method of claim 1 wherein step d) comprises introducing the first and second plasmids into the same cell by mating a first and second yeast cell, wherein the first yeast cell has been transformed with either the first or second plasmid, and wherein the second yeast cell has been transformed with the first or second plasmid with which the first yeast cell was not transformed.

5. The method of claim 1, wherein in step e) the cell into which the first and second plasmids are introduced is selected for by interaction of proteins encoded by the first and second cDNAs, wherein the interaction induces expression of a selectable marker, wherein the expression of the selectable marker permits the cell to survive.

6. The method of claim 5, wherein the selectable marker is selected from the group consisting of LEU2, URA3, HIS3, TRP1, ADE2 and LYS2.

* * * * *

SEQUENCE LISTING

<160> NUMBER OF SEQ ID NOS: 23

<210> SEQ ID NO 1
<211> LENGTH: 48
<212> TYPE: DNA
<213> ORGANISM: Artificial Sequence -continued

```
<220> FEATURE:
<221> NAME/KEY: n
<222> LOCATION: 43-48
<223> OTHER INFORMATION: n is g,a,t or c; pAct2 lox71 MAGE/6 Primer

<400> SEQUENCE: 1
gtatagcata cattatacga acggtaaccc tctgagctgg agnnnnnn                48

<210> SEQ ID NO 2
<211> LENGTH: 48
<212> TYPE: DNA
<213> ORGANISM: artificial sequence
<220> FEATURE:
<221> NAME/KEY: n
<222> LOCATION: 43-48
<223> OTHER INFORMATION: n is g,a,t or c; PCD2 lox66 MAGE/6 Primer

<400> SEQUENCE: 2
cgtataatgt atgctatacg aacggtaccc tctgagctgg agnnnnnn                48

<210> SEQ ID NO 3
<211> LENGTH: 40
<212> TYPE: DNA
<213> ORGANISM: artificial sequence
<220> FEATURE:
<221> NAME/KEY: n
<222> LOCATION: 35-40
<223> OTHER INFORMATION: n is g,a,t or c; Lox71 MmeI primer

<400> SEQUENCE: 3
tataatgtat gctatacgaa cggtaggatc caacnnnnnn                        40

<210> SEQ ID NO 4
<211> LENGTH: 38
<212> TYPE: DNA
<213> ORGANISM: artificial sequence
<220> FEATURE:
<221> NAME/KEY: n
<222> LOCATION: 33-38
<223> OTHER INFORMATION: n is g,a,t or c; Lox66 MmeI primer

<400> SEQUENCE: 4
catatcgtat gtaatatgct tgccataggt tgnnnnnn                          38

<210> SEQ ID NO 5
<211> LENGTH: 529
<212> TYPE: DNA
<213> ORGANISM: artificial sequence
<220> FEATURE:
<221> NAME/KEY: n
<222> LOCATION: 392, 448, 453, 455, 473, 476, 479, 505,
       522, 524, 528
<223> OTHER INFORMATION: n is a, g, t, c; concatamerized sequence tags

<400> SEQUENCE: 5
atccccgggg ctgcaggaat tcgatgcgat aataaccacg gccaccactg             50
gagggatccc ttgatcagac accactggag cacgagaaga aggagccacc            100
actggagcac gagaagaagg agctcaccac tggagggatc ccttgatcag            150
acaccactgg aggggtcgg gacggagaca ccactggagg agggcacagc             200
agaagcacca ctgagggtg gggactttct cccaccactg gagggatccc             250
ttgatcatac accactggag aggtcccga tgctggcacc actggagcct             300
cgatcagatc tgccaccact ggagcactag aaaaagagga caccactgga            350
ggagggcaca gcagaagcac cactggaggg tggggacttt cntcccacca            400
```

| | |
|---|---|
| ctggagtgct cgttagaata ttcaccactg gagggatccc ttgatcanac | 450 |
| acntnctgga gcggacagag ganacntcna ccactggagc ggcaggggaa | 500 |
| cttancccca cttgggacca cnanaagna | 529 |

```
<210> SEQ ID NO 6
<211> LENGTH: 16
<212> TYPE: DNA
<213> ORGANISM: mouse
<220> FEATURE:
<223> OTHER INFORMATION: mouse cDNA sequence tag

<400> SEQUENCE: 6
```

| | |
|---|---|
| cgataataac cacggc | 16 |

```
<210> SEQ ID NO 7
<211> LENGTH: 16
<212> TYPE: DNA
<213> ORGANISM: mouse
<220> FEATURE:
<223> OTHER INFORMATION: mouse cDNA sequence tag

<400> SEQUENCE: 7
```

| | |
|---|---|
| ggatcccttg atcaga | 16 |

```
<210> SEQ ID NO 8
<211> LENGTH: 16
<212> TYPE: DNA
<213> ORGANISM: mouse
<220> FEATURE:
<223> OTHER INFORMATION: mouse cDNA sequence tag

<400> SEQUENCE: 8
```

| | |
|---|---|
| cacgagaaga aggagc | 16 |

```
<210> SEQ ID NO 9
<211> LENGTH: 17
<212> TYPE: DNA
<213> ORGANISM: mouse
<220> FEATURE:
<223> OTHER INFORMATION: mouse cDNA sequence tag

<400> SEQUENCE: 9
```

| | |
|---|---|
| cacgagaaga aggagct | 17 |

```
<210> SEQ ID NO 10
<211> LENGTH: 16
<212> TYPE: DNA
<213> ORGANISM: mouse
<220> FEATURE:
<223> OTHER INFORMATION: mouse cDNA sequence tags

<400> SEQUENCE: 10
```

| | |
|---|---|
| ggatcccttg atcaga | 16 |

```
<210> SEQ ID NO 11
<211> LENGTH: 16
<212> TYPE: DNA
<213> ORGANISM: mouse
<220> FEATURE:
<223> OTHER INFORMATION: mouse cDNA sequence tag

<400> SEQUENCE: 11
```

| | |
|---|---|
| ggggtcggga cggaga | 16 |

<210> SEQ ID NO 12
<211> LENGTH: 16
<212> TYPE: DNA
<213> ORGANISM: mouse
<220> FEATURE:
<223> OTHER INFORMATION: mouse cDNA sequence tag

<400> SEQUENCE: 12
gagggcacag cagaag                                                    16

<210> SEQ ID NO 13
<211> LENGTH: 16
<212> TYPE: DNA
<213> ORGANISM: mouse
<220> FEATURE:
<223> OTHER INFORMATION: mouse cDNA sequence tag

<400> SEQUENCE: 13
ggtggggact ttctcc                                                    16

<210> SEQ ID NO 14
<211> LENGTH: 16
<212> TYPE: DNA
<213> ORGANISM: mouse
<220> FEATURE:
<223> OTHER INFORMATION: mouse cDNA sequence tag

<400> SEQUENCE: 14
ggatcccttg atcata                                                    16

<210> SEQ ID NO 15
<211> LENGTH: 16
<212> TYPE: DNA
<213> ORGANISM: mouse
<220> FEATURE:
<223> OTHER INFORMATION: mouse cDNA sequence tag

<400> SEQUENCE: 15
agggtcccga tgctgg                                                    16

<210> SEQ ID NO 16
<211> LENGTH: 16
<212> TYPE: DNA
<213> ORGANISM: mouse
<220> FEATURE:
<223> OTHER INFORMATION: mouse cDNA sequence tag

<400> SEQUENCE: 16
cctcgatcag atctgc                                                    16

<210> SEQ ID NO 17
<211> LENGTH: 16
<212> TYPE: DNA
<213> ORGANISM: mouse
<220> FEATURE:
<223> OTHER INFORMATION: mouse cDNA sequence tag

<400> SEQUENCE: 17
cactagaaaa agagga                                                    16

<210> SEQ ID NO 18
<211> LENGTH: 16
<212> TYPE: DNA
<213> ORGANISM: mouse
<220> FEATURE:
<223> OTHER INFORMATION: mouse cDNA sequence tag

```
<400> SEQUENCE: 18
gagggcacag cagaag                                                    16

<210> SEQ ID NO 19
<211> LENGTH: 17
<212> TYPE: DNA
<213> ORGANISM: mouse
<220> FEATURE:
<221> NAME/KEY: n
<222> LOCATION: 14
<223> OTHER INFORMATION: n is g,t,a or c; mouse cDNA sequence tag

<400> SEQUENCE: 19
ggtggggact ttcntcc                                                   17

<210> SEQ ID NO 20
<211> LENGTH: 16
<212> TYPE: DNA
<213> ORGANISM: mouse
<220> FEATURE:
<223> OTHER INFORMATION: mouse cDNA sequence tag

<400> SEQUENCE: 20
tgctcgttag aatatt                                                    16

<210> SEQ ID NO 21
<211> LENGTH: 16
<212> TYPE: DNA
<213> ORGANISM: mouse
<220> FEATURE:
<221> NAME/KEY: n
<222> LOCATION: 15
<223> OTHER INFORMATION: n is g,t,a or c; mouse cDNA sequence tag

<400> SEQUENCE: 21
ggatcccttg atcana                                                    16

<210> SEQ ID NO 22
<211> LENGTH: 16
<212> TYPE: DNA
<213> ORGANISM: mouse
<220> FEATURE:
<221> NAME/KEY: n
<222> LOCATION: 12, 15
<223> OTHER INFORMATION: n is g,t,a or c; mouse cDNA sequence tag

<400> SEQUENCE: 22
cggacagagg anacnt                                                    16

<210> SEQ ID NO 23
<211> LENGTH: 16
<212> TYPE: DNA
<213> ORGANISM: mouse
<220> FEATURE:
<221> NAME/KEY: n
<222> LOCATION: 16
<223> OTHER INFORMATION: n is g,t,a or c; mouse cDNA sequence tags

<400> SEQUENCE: 23
cggcagggga acttan                                                    16
```